United States Patent [19]
Baroni et al.

[11] Patent Number: 6,034,090
[45] Date of Patent: Mar. 7, 2000

[54] 1-PHENYLALKYL-1,2,3,6-TETRAHYDROPYRIDINES FOR TREATING ALZHEIMER'S DISEASE

[75] Inventors: Marco Baroni, Vanzago; Rosanna Cardamone, Como, both of Italy; Jacqueline Fournier, Plaisance Du Touch, France; Umberto Guzzi, Milan, Italy

[73] Assignee: Sanofi-Synthlabo, Paris, France

[21] Appl. No.: 09/331,006

[22] PCT Filed: Dec. 12, 1997

[86] PCT No.: PCT/FR97/02286

§ 371 Date: Jul. 27, 1999

§ 102(e) Date: Jul. 27, 1999

[87] PCT Pub. No.: WO98/25903

PCT Pub. Date: Jun. 18, 1998

[30] Foreign Application Priority Data

Dec. 13, 1996 [FR] France .................... 96 15335

[51] Int. Cl.[7] ........................ A61K 31/44; C07D 211/70; C07D 211/72; C07D 213/22
[52] U.S. Cl. .................... 514/277; 514/332; 514/357; 546/255; 546/339; 546/346; 546/329; 546/340; 546/257
[58] Field of Search .................... 546/257, 346, 546/339, 329, 258; 514/277, 357

[56] References Cited

U.S. PATENT DOCUMENTS

| 3,954,871 | 5/1976 | Buu-Hoi et al. | 260/570.6 |
|---|---|---|---|
| 5,109,005 | 4/1992 | Croci et al. | 514/277 |
| 5,229,389 | 7/1993 | Coude et al. | 514/260 |
| 5,270,320 | 12/1993 | Coude et al. | 514/277 |

Primary Examiner—Zinna Northington Davis
Assistant Examiner—Binta Robinson
Attorney, Agent, or Firm—Michael D. Alexander

[57] ABSTRACT

The invention relates to compounds of the formula

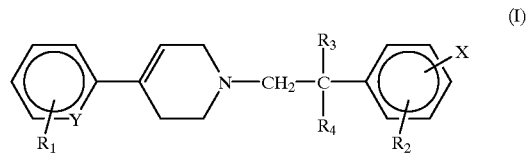

(I)

in which: Y is —CH— or —N—; $R_1$ is hydrogen, a halogen or a $CF_3$, $(C_1-C_4)$alkyl or $(C_1-C_4)$alkoxy group; $R_2$ is a methyl or ethyl group; $R_3$ and $R_4$ are each hydrogen or a $(C_1-C_3)$alkyl; and X is:

(a) a $(C_1-C_6)$alkyl, a $(C_1-C_6)$alkoxy, a $(C_3-C_7)$carboxyalkyl, a $(C_1-C_4)$alkoxy-carbonyl$(C_1-C_6)$alkyl, a $(C_3-C_7)$carboxyalkoxy or a $(C_1-C_4)$alkoxycarbonyl-$(C_1-C_6)$alkoxy;

(b) a radical selected from $(C_3-C_7)$cycloalkyl, $(C_3-C_7)$cycloalkoxy, $(C_3-C_7)$-cycloalkylmethyl, $(C_3-C_7)$cycloalkylamino and cyclohexenyl, it being possible for said radical to be substituted by a halogen, hydroxyl, $(C_1-C_4)$-alkoxy, carboxyl, $(C_1-C_4)$alkoxycarbonyl, amino or mono- or di-$(C_1-C_4)$-alkylamino; or (c) a group selected from a phenyl, phenoxy, phenylamino, N-$(C_1-C_3)$alkyl-phenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkyl-amino, $(C_1-C_4)$acylamino, carboxyl, $(C_1-C_4)$alkoxycarbonyl, aminocarbonyl, mono- or di-$(C_1-C_4)$alkylaminocarbonyl, amino $(C_1-C_4)$alkyl, hydroxy$(C_1-C_4)$alkyl or halogeno $(C_1-C_4)$alkyl;

to a method of preparing them and to the pharmaceutical compositions containing them. These compounds have neurotrophic and neuroprotective activity.

20 Claims, No Drawings

1-PHENYLALKYL-1,2,3,6-TETRAHYDROPYRIDINES FOR TREATING ALZHEIMER'S DISEASE

CROSS REFERENCE TO RELATED APPLICATIONS

This application is a filing under 35 U.S.C. §371 corresponding to International Application Ser. No. PCT/FR97/02286, filed Dec. 12, 1997, which claims priority of FR 96 15335, filed Dec. 13. 1996.

1-Phenylalkyl-1,2,3,6-tetrahydropyridines

The present invention relates to novel 4-substituted 1-phenylalkyl-1,2,3,6-tetrahydropyridines with neurotrophic and neuroprotective activity, to a method of preparing them and to pharmaceutical compositions containing them.

EP-0 458 696 describes the use of a 1-(2-naphthylethyl) 4-(3-trifluoro-methylphenyl)-1,2,3,6tetrahydropyridine for the preparation of drugs intended for the treatment of cerebral and neuronal disorders.

WO 93/11107 describes piperidines and tetrahydropyridines with protective activity against the damage caused by hypoxic/ischemic states.

It has now been found that certain phenylalyl-1,2,3,6-tetrahydropyridines substituted by a phenyl or pyridyl group exert a neurotrophic action on the nervous system which is similar to the action of nerve growth factor (NGF), and can restore the function of damaged cells or cells exhibiting anomalies in their physiological functions.

According to one of its features, the present invention therefore relates to the compounds of formula (I):

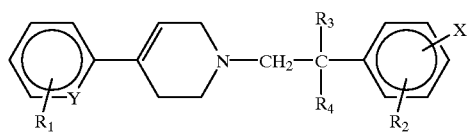

(I)

in which:

Y is —CH— or —N—;

$R_1$ is hydrogen, a halogen or a $CF_3$, $(C_1-C_4)$alkyl or $(C_1-C_4)$alkoxy group;

$R_2$ is a methyl or ethyl group;

$R_3$ and $R_4$ are each hydrogen or a $(C_1-C_3)$alkyl; and

X is:
  (a) a $(C_1-C_6)$alkyl, a $(C_1-C_6)$alkoxy, a $(C_3-C_7)$ carboxyalkyl, a $(C_1-C_4)$alkoxy-carbonyl($C_1-C_6$) alkyl, a $(C_3-C_7)$carboxyalkoxy or a $(C_1-C_4)$ alkoxycarbonyl-$(C_1-C_6)$alkoxy;
  (b) a radical selected from $(C_3-C_7)$cycloalkyl, $(C_3-C_7)$ cycloalkoxy, $(C_3-C_7)$-cycloalkylmethyl, $(C_3-C_7)$ cycloalkylamino and cyclohexenyl, it being possible for said radical to be substituted by a halogen, hydroxyl, $(C_1-C_4)$-alkoxy, carboxyl, $(C_1-C_4)$ alkoxycarbonyl, amino or mono- or di-$(C_1-C_4)$-alkylamino; or
  (c) a group selected from a phenyl, phenoxy, phenylamino, N-$(C_1-C_3)$alkyl-phenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkyl-amino, $(C_1-C_4)$acylamino, carboxyl, $(C_1-C_4)$ alkoxycarbonyl, aminocarbonyl, mono- or di-$(C_1-C_4)$alkylaminocarbonyl, amino($C_1-C_4$)alkyl, hydroxy($C_1-C_4$)alkyl or halogeno($C_1-C_4$)alkyl;

and their salts and solvates and their quaternary ammonium salts.

In the present description the term "$(C_1-C_3)$alkyl" denotes methyl, ethyl, n-propyl and i-propyl groups.

The term "$(C_1-C_4)$alkyl" denotes methyl, ethyl, n-propyl, i-propyl, n-butyl, i-butyl, s-butyl and 1-butyl groups.

The term "$(C_1-C_6)$alkyl" denotes a hydrocarbon radical containing from 1 to 6 carbon atoms, for example methyl, ethyl, n-propyl, i-propyl, n-butyl, i-butyl, s-butyl, t-butyl, n-pentyl, i-pentyl, neopentyl, t-pentyl, n-hexyl, i-hexyl, etc.

The term "alkoxy" denotes a hydroxyl group substituted by a $(C_1-C_6)$alkyl, advantageously $(C_1-C_4)$alkyl and preferably $(C_1-C_3)$alkyl group.

If X is a phenyl group, the nomenclature used for the biphenylyl radical is in accordance with the IUPAC rules, i.e. the positions of the two rings are numbered as follows:

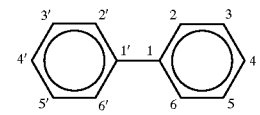

and the radicals of this structure have the following names:

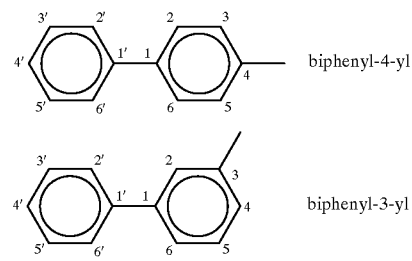

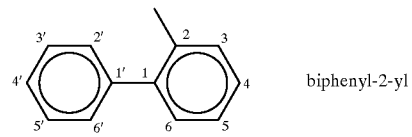

Among the compounds of formula (I) in which X is a group (c), one preferred group is represented by the compounds in which the phenyl is substituted by 1 to 3 halogens, 1 to 3 $CF_3$, 1 to 3 $(C_1-C_4)$alkyl, 1 to 3 $(C_1-C_4)$alkoxy, 1 to 3 cyano, 1 to 3 amino, 1 to 3 mono- or di-$(C_1-C_4)$ alkylamino, 1 to 3 $(C_1-C_4)$-acylamino, 1 to 3 carboxyl, 1 to 3 $(C_1-C_4)$alkoxycarbonyl, 1 to 3 aminocarbonyl, 1 to 3 mono- or di-$(C_1-C_4)$alkylaminocarbonyl, 1 to 3 amino($C_1-C_4$)alkyl, 1 to 3 hydroxy($C_1-C_4$)alkyl or 1 to 3 halogeno ($C_1-C_4$)alkyl.

Another preferred group consists of the compounds of formula (I) in which Y is a group —CH— and $R_1$ is $CF_3$.

Another preferred group consists of the compounds of formula (I) in which Y is a nitrogen atom and $R_1$ is a chlorine atom.

Another preferred group consists of the compounds of formula (I) in which X is a $(C_1-C_6)$alkyl group, especially ethyl.

Particularly advantageous compounds are represented by formula (I'):

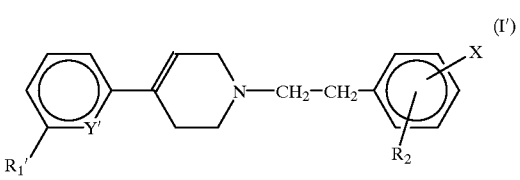

in which $R_1'$ is $CF_3$ and Y' is CH, or $R_1'$ is Cl and Y' is N, $R_2$ and X being as defined above, and their salts, solvates and quaternary ammonium salts.

Another preferred group consists of the compounds of formula (I') in which X is a $(C_1-C_6)$alkyl group.

Particularly advantageous compounds according to the present invention are as follows: 1-[2-(3,4-diethylphenyl) ethyl]-4-(3-trirluoromethylphenyl)-1,2,3,6-tetrahydropyridine, 1-[2-(3-methyl-4-pentylphenyl)ethyl]-4-(3-trifluoromethyl-phenyl)-1,2,3,6-tetrahydropyridine, 1-[2-(4-methyl-3-pentylphenyl)ethyl]-4-(3-trifluoromethyylphenyl)-1,2,3,6-tetrahydroipyridine, 1-[2-(3,4-diethylphenyl)ethyl]-4-(6-chloropyrid-2-yl)-1,2,3,6-tetrahydropyridine and their salts, solvates and quaternary ammonium salts.

According to another of its features, the present invention relates to a method of preparing the compounds of formula (I), their salts or solvates and their quaternary ammonium salts, characterized in that:

(a) an aryl-1,2,3,6-tetrahydropyridine of formula (II):

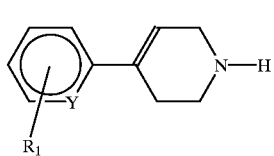

in which Y and $R_1$ are as defined above, is reacted with a compound of formula (III):

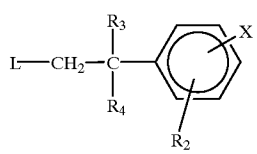

in which $R_2$, $R_3$, $R_4$ and X are as defined above and L is a leaving group, for example a chlorine, bromine or iodine atom or the methanesulfonyloxy, p-toluenesulfonyloxy or trifluoromethanesulfonyloxy group; and (b) the resulting compound of formula (I) is isolated and optionally converted to one of its salts or solvates or one of its quaternary ammonium salts.

The reaction is carried out in an organic solvent at a temperature between room temperature and the reflux temperature of the solvent used.

An aliphatic alcohol having from 1 to 6 carbon atoms, such as methanol, ethanol, isopropanol, n-butanol or n-pentanol, is preferably used as the organic solvent, but it is also possible to use other solvents such as hexane, dimethyl-formamide, dimethyl sulfoxide, sulfolane, acetonitrile, pyridine and the like.

The reaction is advantageously carried out in the presence of a basic agent such as an alkali metal carbonate or triethylamine, especially if L is a halogen atom.

The reaction temperature can vary between room temperature (about 20° C.) and the reflux temperature, the reaction times varying accordingly. In general, after refluxing for 6 to 12 hours, the reaction has ended and the final product obtained can be isolated according to the conventional techniques in the form of the free base or one of its salts, the free base optionally being converted to one of its salts by simple salification in an organic solvent such as an alcohol, preferably ethanol or isopropanol, an ether such as 1,2-dimethoxyethane, ethyl acetate, acetone or a hydrocarbon like hexane.

The compound of formula (I) obtained is isolated according to the conventional techniques and optionally converted to one of its acid addition salts; alternatively, if an acid group is present, the amphoteric character of the compound enables the salts to be separated either with acids or with bases.

If the salts of the compound of formula (I) are prepared for administration as drugs, the acids or bases employed must be pharmaceutically acceptable; if salts of the compound of formula (I) are prepared for another purpose, for example to improve the purification of the product or to improve analytical assays, any acid or base may then be used.

Examples of the salts with pharmaceutically acceptable acids are those with mineral acids, such as the hydrochloride, hydrobromide, borate, phosphate, sulfate, hydrogensulfate, hydrogenphosphate and dihydrogenphosphate, and those with organic acids, such as the citrate, benzoate, ascorbate, methylsulfate, naphthalene-2-sulfonate, picrate, fumarate, maleate, malonate, oxalate, succinate, acetate, tartrate, mesylate, tosylate, isethionate, α-ketoglutarate, α-glycerophosphate, glucose-1-phosphate, etc.

Examples of the salts with pharmaceutically acceptable bases of the compounds of formula (I) in which the substituent X contains a carboxyl are those with alkali metals or alkaline earth metals such as sodium, potassium, calcium and magnesium, and those with organic bases such as amines, basic amino acid, (lysine, arginine, histidine), trometamol, N-methylglucamine, etc.

The starting amines of formula (II) in which Y is CH are known compounds or they can be prepared by methods analogous to those used to prepare the known compounds.

The starting amines of formula (II) in which Y is N can be prepared by reacting the appropriate 2-halogenopyridine of formula (p):

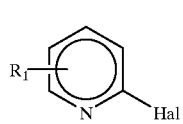

in which $R_1$ is as defined above and Hal is a halogen atom, with a 1,2,3,6-tetrahydropyridine of formula (q):

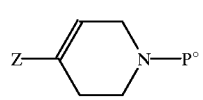

in which P° is a protecting group, for example the benzyl group, and Z is a substituent which allows the nucleophilic substitution of the pyridine halogen. Examples of such substituents are trialkylstannanes such as tributylstannane, or Grignard compounds.

The 1,2,3,6-tetrahydropyridine is then deprotected by cleavage of the protecting group under appropriate conditions.

The compounds of formula (III) can be prepared:

either by reacting the appropriate benzene of formula (r):

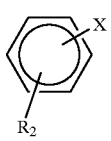

(r)

in which $R_2$ and X are as defined above, with an acyl halide of the formula L—$CH_2$—CO—Hal, in which L and Hal are as defined above, in the presence of a Lewis acid, according to the well-known Friedel-Crafts reaction, and by reducing the resulting ketone of formula (s):

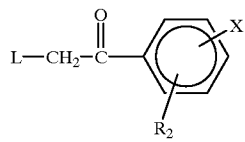

(s)

according to the procedures widely described in the literature, in order to prepare a compound of formula (III) in which $R_3=R_4=H$;

or by reducing the acids of formula (V):

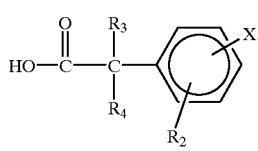

(V)

in which $R_2$, $R_3$, $R_4$ and X are as defined above, to the alcohol and then converting the hydroxyl group to a leaving group.

The acids of formula (V) are generally compounds which have been described in the literature or they can be prepared analogously.

Preparatory Examples are also given in the experimental section.

The activity of the compounds of formula (I) on the nervous system was demonstrated in in vitro and in vivo studies according to the methods described in EP-0 458 696 and, for evaluation of the neuronal survival, with the aid of an in vitro survival test carried out using neurons isolated from dissections of the septal region of rat embryos.

In this test the septal region of 17- to 18-day-old rat embryos is removed under a dissecting microscope under sterile conditions and then dissociated in a trypsin/EDTA medium. The cellular suspension is placed in a culture flask in a DME/Ham's F12 (v:v) medium (Dulbecco Modified Eagle's medium/Ham's F12 nutrient mixture—R. G. Ham, Proc. Nat. Sci., 1965, 53, 288) containing 5% of calf serum and 5% of horse serum, and is kept at 37° C. for 90 minutes. This treatment makes it possible to remove the non-neuronal cells.

The neuroblasts are then inoculated at a rate of $17\times10^4$ cells/cm$^2$ into a non-serum culture medium consisting of DME/Ham's F12 medium containing selenium (30 nM) and transferrin (1.25 $\mu$M) in the wells of a titer plate. Each well has been treated with poly-L-lysine beforehand. The inoculated plates are placed in an incubator in the oven (37° C.; 5% $CO_2$).

The test compounds are dissolved in DMSO and diluted with the culture medium as required.

The neuroblasts are kept in plates containing the test compound or the corresponding solvent for 4 days without the medium being changed.

After 4 days the medium is replaced with a tetrazolium salt dissolved in the culture medium (0.15 mg/ml). The cells are then placed in the oven at 37° C. for 4 hours. The mitochondrial succinate dehydrogenases of the living cells reduce the tetrazolium salt to formazan blue, whose optical density is measured at 540 mn after dissolution in DMSO. This density has a linear correlation with the number of living cells (Manthorpe et al., Dev. Brain Res., 1988, 2, 191–198).

The difference between the groups containing the test compounds and the controls was evaluated by statistical analysis using the two-tailed Dunnett t-test.

In said test the compounds of formula (I) were found to be as active as or more active than the compounds described in EP-0 458 696, the efficacy of certain compounds of formula (I) in respect of neuronal survival being twice that of compound A described in EP-0 458 696.

By virtue of this potent neuroprotective activity and their low toxicity compatible with use as drugs, the compounds of formula (I) and their pharmaceutically acceptable addition salts, their solvates and their quaternary ammonium salts can be used for the preparation of pharmaceutical compositions indicated in the treatment and/or prophylaxis of all diseases involving neuronal degeneration. More particularly, the compounds of the invention can be used, either by themselves or in co-administration or association with other active principles acting on CNS, for example acetylcholinesterase inhibitors, selective Ml cholinomimetics, NMDA antagonists and nootropics such as piracetam, especially in the following indications: memory disorders, vascular dementia, postencephalitic disorders, postapoplectic disorders, post-traumatic syndromes due to a cranial traumatism, disorders deriving from cerebral anoxia, Alzheimer's disease, senile dementia, subcortical dementia such as Huntington's chorea and Parkinson's disease, dementia caused by AIDS, neuropathies deriving from morbidity or damage to the sympathetic or sensory nerves, and brain diseases such as cerebral edema, spinocerebellar degenerations and motor neuron degenerations, for example amyotrophic lateral sclerosis.

The compounds of the invention can conveniently be administered orally, parenterally, sublingually or transdermally. The amount of active principle to be administered in the treatment of cerebral and neuronal disorders according to the method of the present invention depends on the nature and severity of the complaints to be treated and on the weight of the patients. Nevertheless the preferred unit doses will generally comprise from 0.25 to 700 mg, advantageously from 0.5 to 300 mg and preferably from 1 to 150 mg, for example between 2 and 50 mg, i.e. 2, 5, 10, 15, 20, 25 or 50 mg of product. These unit doses will normally be administered one or more times a day, for example 2, 3, 4 or 5 times a day and preferably one to three times a day, the overall dose in man varying between 0.5 and 1400 mg per day, advantageously between 1 and 900 mg per day, for example from 2 to 500 mg and more conveniently from 2 to 200 mg per day.

According to another of its features, the present invention relates to a pharmaceutical composition containing, as active principles, a compound of formula (I) above and a compound indicated in the symptomatic treatment of senile dementia of the Alzheimer type (DAT), or their pharmaceutically acceptable salts.

The expression "compound indicated in the symptomatic treatment of senile dementia of the Alzheimer type (DAT)" indicates a product which is capable of improving the symptomatological picture of patients suffering from DAT, without acting on the causes of the disease.

Examples of such compounds are acetylcholinesterase inhibitors, $M_1$ muscarinic agonists, nicotinic agonists, NMDA receptor antagonists and nootropics.

Preferred acetylcholinesterase inhibitors are donepezil and tacrine.

Examples of other acetylcholinesterase inhibitors which can be used are rivastigmine (SDZ-ENA-713), galanthamine, metrifonate, eptastigmine, velnacrine and physostigmine (Drugs, 1997, 53(5), 752–768; The Merck Index, 12th edition).

Other acetylcholinesterase inhibitors are 5,7-dihydro-3-[2-[1-(phenyl-methyl)-4-piperidinyl]ethyl]-6H-pyrrolo[3,2-f]-1,2-benzisoxazol-6-one, also called icopezil (J. Med. Chem., 1995, 38, 2802–2808), MDL-73,745 or zifrosilone (Eur. J. Pharmacol., 1995, 276, 93–99) and TAK-147 (J. Med. Chem., 1994, 37 2292–2299).

Examples of other acetylcholinesterase inhibitors are those described in patent applications JP 09-095483, WO 97/13754, WO 97/21681, WO 97/19929, ZA 96-04565, U.S. Pat. No. 5,455,245, WO 95-21822, EP 637 586, U.S. Pat. No. 5,401,749, EP 742 207, U.S. Pat. No. 5,547,960, WO 96/20176, WO 96/02524, EP 677 516, JP 07-188177, JP 07-133274, EP 649 846, EP 648 771, JP 07-048370, U.S. Pat. No. 5,391,553, WO 94/29272 and EP 627 400.

According to another of its features, the present invention relates to a pharmaceutical composition containing, as active principles, a compound of formula (I) and an $M_1$ receptor agonist or their pharmaceutically acceptable salts.

Examples of $M_1$ receptor agonists are milameline, besipiridine, talsaclidine, xanomeline, YM-796 and YM-954 (Eur. J. Pharmacol., 1990, 187, 479–486), 3-[N-(2-diethylamino-2-methylpropyl)-6-phenyl-5-propyl]pyridazinamine, also called SR-46559 (Biorg. Med. Chem. Let., 1992, 2, 833–838), AF-102, CI-979, L-689,660, LU 25-109, S-9977-2, SB 202,026, thiopilocarpine and WAL 2014 (Pharmacol. Toxicol., 1996, 78, 59–68).

According to another of its features, the invention relates to a pharmaceutical composition containing, as active principles, a compound of formula (I) and a nicotinic agonist or their pharmaceutically acceptable salts.

Examples of advantageous nicotinic agonists are MKC-231 (Biorg. Med. Chem. Let., 1995, 5(14), 1495–1500), T-588 (Japan J. Pharmacol., 1993, 62, 81–86) and ABT-418 (Br. J. Pharmacol., 1997, 120, 429–438).

According to another of its features, the invention relates to a pharmaceutical composition containing, as active principles, a compound of formula (I) and an NMDA receptor antagonist or their pharmaceutically acceptable salts.

An example of an advantageous NMDA receptor antagonist is memantine (Arzneim. Forsch., 1991, 41, 773–780).

According to another of its features, the invention relates to a pharmaceutical composition containing, as active principles, a compound of formula (I) and a nootropic agent or their pharmaceutically acceptable salts.

Examples of nootropic agents which can be used according to the invention are netiracetam and nebracetam (Merck Index, 12th edition).

The doses of the two associated active principles are generally chosen from the doses of each drug which would be administered in monotherapy.

According to a further feature, the present invention also relates to a method of treating senile dementia of the Alzheimer type, which consists in administering, to a patient suffering from this disease, an effective dose of a compound of formula (I) or one of its pharmaceutically acceptable salts and an effective dose of a compound indicated in the symptomatic treatment of DAT, or one of its pharmaceutically acceptable salts, said compounds being administered simultaneously, sequentially or spread over a period of time and it being possible for the effective doses of the active principles to be contained in separate unit forms of administration; alternatively, if the two active principles are administered simultaneously, they are advantageously contained in a single pharmaceutical form.

In the pharmaceutical compositions of the present invention for oral, sublingual, subcutaneous, intramuscular, intravenous, transdermal or rectal administration, the active principle can be administered to animals and humans in unit forms of administration, either as such, for example in lyophilized form, or mixed with conventional pharmaceutical carriers, for the treatment of the above-mentioned complaints. The appropriate unit forms of administration include oral forms such as tablets, which may be divisible, gelatin capsules, powders, granules and solutions or suspensions to be taken orally, sublingual and buccal forms of administration, subcutaneous, intramuscular or intravenous forms of administration, local forms of administration and rectal forms of administration.

When a solid composition in the form of tablets is prepared, the main active ingredient is mixed with a pharmaceutical vehicle such as gelatin, starch, lactose, magnesium stearate, talcum, gum arabic or the like. The tablets can be coated with sucrose or other appropriate substances or they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methyl-paraben and propylparaben as antiseptics, a flavoring and an appropriate color.

Water-dispersible powders or granules can contain the active ingredient mixed with dispersants or wetting agents, or with suspending agents such as polyvinylpyrrolidone, and with sweeteners or taste correctors.

Rectal administration is effected using suppositories, which are prepared with binders melting at the rectal temperature, for example cocoa butter or polyethylene glycols.

Parenteral administration is effected using aqueous suspensions, saline solutions or injectable sterile solutions containing pharmacologically compatible dispersants-and/or wetting agents, for example propylene glycol or butylene glycol.

The active principle can also be formulated as microcapsules, optionally wit one or more carriers or additives.

In the pharmaceutical compositions according to the present invention, the active principle can also be in the form of an inclusion complex in cyclodextrins, their ethers or their esters.

The Examples which follow illustrate the invention more clearly without however limiting it.

EXAMPLE 1

1-[2-(3,4-Diethylphenyl)ethyl]-4-(3-trifluoromethylphenyl)-1,2,3,6-tetrahydropridine hydrochloride 1a/1-Bromo-2-(3,4-diethylphenyl)ethane A mixture of 4.4 g (0.033 mol) of 3,4-diethylbenzene, 50 ml of methylene chloride and 8.8 g (0.044 mol) of bromoacetyl bromide is cooled to 0–5° C. and 5.0 g (0.037 mol) of aluminum trichloride are added. The mixture is stirred at 0–5° C. for one hour and then left to stand overnight at room temperature. It is poured into a water/ice mixture and extracted with methylene chloride, the organic phase is dried over sodium sulfate and the solvent is evaporated off under reduced pressure. 2.9 g (0.011 mol) of the resulting oil are mixed with 6 ml (0.079 mol) of trifluoroacetic acid and 6.7 ml (0.057 mol) of triethylsilane and the mixture is heated at 80° C. for 4 hours.

A saturated aqueous sodium bicarbonate solution is then added until the pH is basic, the mixture is extracted with ethyl ether, the organic phase is dried over sodium sulfate and the solvent is evaporated off under reduced pressure. The resulting crude oil is purified by chromatography on a silica gel column using cyclohexane as the eluent to give the title compound.

1b/1-[2-(3,4-Diethylphenyl)ethyl]-4-(3-tnifluoromethylphenyl)-1,2,3,6-tetra-hydropyridine hydrochloride A mixture of 2.6 g (0.001 mol) of 4(3-trifluoromethylphenyl)-1,2,3,6-tetra-hydropyridine, 60 ml of butanol, 4.1 g (0.025 mol) of anhydrous potassium carbonate chips and 2.6 g (0.00113 mol) of the product of the previous step is refluxed for 5 hours. The solvent is evaporated off under reduced pressure, the residue is taken up with ethyl acetate, washed with water and dried over sodium sulfate and the solvent is evaporated off under reduced pressure. The hydrochloride of the resulting oil is prepared by treatment with a saturated solution of hydrochloric acid in isopropanol to give 1.6 g of the title compound. M.p. 220–222° C.

EXAMPLE 2

1-[2-(3-Methyl-4-pentylphenyl)ethyl]-4-(3-trifluoromethylphenyl)-1,2,3,6-tetrahydropyridine and 1-[2-(4-methyl-3-pentylphenyl)ethyl]-4-(3-trifluoromethylphenyl)-1,2,3,6-tetrahydropyridine and their oxalates 2a/1-Methyl-2-pentylbenzene 4.7 g (0.035 mol) of phthalaldehyde are added dropwise to a solution of 50 ml (0.1 mol) of a 2 M solution of n-butylmagnesium chloride in TEF under a nitrogen atmosphere. The mixture warms up spontaneously to 40–45° C. It is stirred at room temperature for one hour and poured into a saturated ammonium chloride solution. The mixture is extracted with ethyl ether, washed with water and dried over sodium sulfate and the solvent is evaporated off under reduced pressure. The resulting oil is purified by chromatography on a silica column using a 7/3 cyclohexane/ethyl acetate mixture as the eluent. The product with the highest Rf is isolated to give 2.0 g of an oil. The crude reaction product is dissolved in 25 ml of ethanol, and 1 ml of concentrated sulfuric acid and 0.15 g of 10% Pd/C are added. The mixture is hydrogenated at room temperature for 7 hours. The catalyst is filtered off, the solvent is evaporated off under reduced pressure and the residue is taken up with ethyl acetate. The mixture is washed with an aqueous sodium bicarbonate solution and dried and the solvent is evaporated off under reduced pressure to give 1.35 g of the title product.

2b/1-Bromo-2-(3-methyl4-pentylphenyl)ethane and 1-bromo-2-(4-methyl-3-pentylphenyl)ethane A mixture of 1.17 g (0.0054 mol) of the product of the previous step and 0.62 ml (0.0072 mol) of bromoacetyl bromide is cooled to 0–5° C. and 0.81 g (0.006 mol) of aluminum trichloride is added. The mixture is stirred at 0–5° C. for one hour and then at room temperature for 4 hours. It is poured onto ice, the two phases are separated, the organic phase is washed with water and dried and the solvent is evaporated off under reduced pressure. The residue is dissolved in 2.9 ml of trifluoroacetic acid, 3.1 ml (0.0267 mol) of triethyl-silane are added and the mixture is heated at 80° C. for 5 hours. It is poured into an aqueous sodium bicarbonate solution and extracted with ethyl ether.

The extract is washed with water and dried over sodium sulfate to give a mixture of the title compounds.

2c/1-[2-(3-Methyl-4-pentylphenyl)ethyl ]-4-(3-trifluoromethylphenyl)-1,2,3,6-tetrahydropyridine and 1-[2-(4-methyl-3-pentylphenyl)ethyl ]-4-(3-trifluoromethylphenyl)-1,2,3,6-tetrahydropyridine and their oxalates.

A mixture of 0.7 g (0.0031 mol) of 4-(3-trifluoromethylphenyl)-1,2,3,6-tetra-hydropyridine, 16 ml of butanol, 0.9 g (0.0065 mol) of anhydrous potassium carbonate chips and the product obtained in the previous step (theoretical amount 0.0054 mol) is refluxed for 6 hours. The solvent is evaporated off under reduced pressure, the residue is taken up with ethyl acetate, washed with water and dried over sodium sulfate and the solvent is evaporated off under reduced pressure. The resulting oil is purified by chromatography on a silica gel column using a 7/3 cyclohexane/ethyl acetate mixture as the eluent. Two products of similar Rf are isolated. The product with the highest Rf corresponds to 1-[2-(3-methyl-4-pentylphenyl)ethyl ]-4 (3-trifluoromethyl-phenyl)-1,2,3,6-tetrahydropyridine. The oxalate is prepared in acetone to give 0.12 g of product. M.p. 140–143° C. The product with the lowest Rf corresponds to the isomer 1-[2-(4-methyl-3-pentylphenyl)ethyl]4(3-trifluoromethylphenyl)-1,2,3,6-tetrahydropyridine. The oxalate is prepared in acetone. The product is crystallized from acetone to give 0.08 g of product. M.p. 167–169° C.

EXAMPLE 3

1-[2-(3,4-Diethylphenyl)ethyl]-4-(6-chloropyrid-2-yl)-1,2,3,6-tetrahydropyridine hydrochloride 3a/(1-Benzyl-1,2,3,6-tetrahydropyrid-4-yl)tributylstannane A mixture of 15.85 g (0.0837 mol) of 1-benzyl-4-piperidone in 140 ml of anhydrous dimethoxyethane and 25 g (0.0837 mol) of trisilidrazine in 140 ml of anhydrous dimethoxyethane is stirred at room temperature for 3 hours. The solvent is evaporated off under reduced pressure. The residue is taken up with 420 ml of anhydrous hexane, and 420 ml of anhydrous tetramethyl-ethylenediamine are added. The mixture is cooled to −78° C. and 156 ml of n-butyllithium (0.25 mol) (1.6 M solution in hexane) are added dropwise. After about 30 minutes, the temperature is allowed to rise to 0° C. and the reaction mixture is stirred for 15 minutes. 45 ml (0.167 mol) of tributylstannane chloride are then added. After 1 hour, a water/ice mixture is added extremely cautiously. After extraction with ethyl ether, the organic phase is washed with water and dried over sodium sulfate and the solvent is evaporated off under reduced pressure to give 70 g of a crude product, which is purified by chromatography on a silica gel column using a 95/5 cyclohexane/ethyl acetate mixture as the eluent to give the title compound in the form of an oil. $^1$H-NMR (CDCl$_3$)—d (ppm): 0.84 (9H; m: CH$_3$); 1.19–1.58 (18H; m: CH$_2$ -chain); 2.31 (2H; m); 2.53 (2H; m); 3.02 (2H; m); 356 (2H; s: benzylic methylene); 5.76 (1H; m*); 7.18–7.41 (5H; m: arom.). * satellite bands $^{3l}$ J$_{cis}$($^1$H-$^{117}$Sn) and $^3$J$_{cis}$($^1$H-$^{119}$Sn).

3b/1-Benzyl4-(6-chloropyrid-2-yl)-1,2,3,6-tetrahydropyridine 18.5 g (0.04 mol) of the compound of the previous step are dissolved in 200 ml of anhydrous dimethylformamide under a nitrogen atmosphere. 11.8 g (0.08 mol) of 2,6-dichloropyridine, 0.64 g of Pd(II)(Ph$_3$P)$_2$Cl$_2$, 4.38 g (0.04 mol) of tetramethylammonium chloride and 2.76 g (0.02 mol) of potassium carbonate are added to the solution. The mixture is heated at 110° C. for 6 hours and then poured into 100 ml of 5% sulfuric acid solution. After extraction with ethyl ether, ammonium hydroxide is added to the aqueous phase until the pH is basic, and extraction is carried out with ethyl acetate.

The combined organic phases are dried over sodium sulfate and the solvent is evaporated off under reduced pressure. The residue is purified by chromatography on a silica gel column using a 1/1 cyclohexane/ethyl acetate mixture as the eluent to give the title compound. M.p. 100–102° C.

3c/4-(6-Chloropyrid-2-yl)-1,2,3,6-tetrahydropyrindne hydrochloride

A solution of 7.0 g (0.024 mol) of the compound of the previous step in 110 ml of dichloroethane is cooled to 0–5° C. and 5.8 ml (0.054 mol) of chloroethyl chloroformate are added. The mixture is stirred for 5 minutes and then refluxed for 1.5 hours. The solvent is evaporated off under reduced pressure and the residue is taken up with 100 ml of methanol and refluxed for 1 hour. The solvent is evaporated off, the residue is taken up with isopropanol and the solid is filtered off to give the title compound, which is crystallized from 90% ethanol. M.p. 305–307° C.

3d/1-[2-(3,4-Diethylphenyt)ethyl]4-(6-chloropyrid-2-yl)-1,2,3,6-tetrahydropyridine hydrochloride The title compound is obtained by the procedure described in Example 1b/except that the product of the previous step is used instead of 4-(3-trifluoromethylphenyl)-1,2,3,6-tetrahydropyridine. M.p. 234–236° C.

EXAMPLES 4–13

The following compounds are obtained by the procedure described in Example 2 except that the appropriate magnesium halide is used:

1-[2-(3-ethyl-4-methylphenyl)ethyl]-4-(3-trifluoromethylphenyl)-1,2,3,6-tetrahydropyridine—Ex. 4

1-[2-(4-ethyl-3-methylphenyl)ethyl]-4-(3-trifluoromethylphenyl)-1,2,3,6-tetrahydropyridine—Ex. 5

1-[2-(3-ethyl4-propylphenyl)ethyl]-4-(3-trifluoromethylphenyl)-1,2,3,6-tetrahydropyridine—Ex. 6

1-[2-(4-ethyl-3-propylphenyl)ethyl]-4-(3-trifluoromethylphenyl)-1,2,3,6-tetrahydropyridine—Ex. 7

1-[2-(3-butyl-4-methylphenyl)ethyl]4-(3-trifluoromethylphenyl)-1,2,3,6-tetrahydropyridine—Ex. 8

1-[2-(4-butyl-3-methylphenyl)ethyl]4-(3-trifluoromethylphenyl)-1,2,3,6-tetrahydropyridine—Ex. 9

1-[2-(3-isobutyl-4-methylphenyl)ethyl]-4-(3-trifluoromethylphenyl)-1,2,3,6-tetrahydropyridine—Ex. 10

1-[2-(4-isobutyl-3-methylphenyl)ethyl]-4-(3-trifluoromethylphenyl)-1,2,3,6-tetrahydropyridine—Ex. 11

1-[2-(3-isobutyl-4-ethylphenyl)ethyl]4-(3-trifluoromethylphenyl)-1,2,3,6-tetrahydropyridine—Ex. 12

1-[2-(4-isobutyl-3-ethylphenyl)ethyl]-4-(3-trifluoromethylphenyl)-1,2,3,6-tetrahydropyridine—Ex. 13

EXAMPLE 14

1-[2-(6-Methylbiphenyl-3-yl)ethyl]-4-(3-trifluoromethylphenyl)-1,2,3,6-tetrahydropyridine The title compound is obtained by the procedure described in Example 2 except that phenyllithium is used instead of n-butylmagnesium chloride.

EXAMPLE 15

1-[2-(3,4-Dimethylphenyl)ethyl]-4-(3-trifluoromethylphenyl)-1,2,3,6-tetrahydropyridine hydrochloride 15a/1-Bromo-2-(3,4-dimethylphenyl)ethane 4.5 g (0.03 mol) of 3,4dimethylacetophenone in 12 ml of methanol are cooled to 0–5° C. and 1.5 ml (0.09 mol) of bromine are added dropwise. The mixture is stirred at room temperature for 24 hours and then left to stand overnight at room temperature. The methanol is evaporated off and the mixture is purified by chromatography on a silica gel column using a 95/5 cyclohexane/ethyl acetate mixture as the eluent. 5.3 g (0.013 mol) of the resulting product are mixed with 12.5 ml (0.162 mol) of trifluoroacetic acid and 18.7 ml (0.011 mol) of triethylsilane and the mixture is heated at 80° C. for 1 hour. A saturated aqueous sodium bicarbonate solution is then added until the pH is basic, the mixture is extracted with ethyl ether, the organic phase is dried over sodium sulfate and the solvent is evaporated off under reduced pressure to give 5.2 g of the title compound.

15b/1-[2-(3,4-Dimethylphenyl)ethyl]-4-(3-trfluoromethyphenyl)-1,2,3,6-tetrahydropyridine hydrochloride A mixture of 1.8 g (0.0068 mol) of 4-(3-trifluoromethylphenyl)-1,2,3,6-tetrahydropyridine, 25 ml of butanol, 2.4 g (0.017 mol) of anhydrous potassium carbonate chips and 2 g (0.0094 mol) of the product of the previous step is refluxed for 6 hours. The solvent is evaporated off under reduced pressure, the residue is taken up with ethyl acetate, washed with water and dried over sodium sulfate and the solvent is evaporated off under reduced pressure. The product is purified by chromatography on a silica gel column using a 7/3 cyclohexane/ethyl acetate mixture as the eluent. The hydrochloride of the resulting oil is prepared by treatment with a saturated solution of hydrochloric acid in isopropanol to give 1.1 g of the title compound. M.p. 270–272° C.

EXAMPLE 16

1-[2-(3,4-Diethylphenyl)ethyl]-4-(2-trifluoromethylphenyt)-1,2,3,6-tetrahydropyridine hydrochloride 16a/4-Hydroxy-4-(2-trifluoromethylphenyl)piperidine hydrochloride 3.25 g (0.135 mol) of Mg are mixed with a spatula tipfull of 12, and a solution of 30.4 g (0.135 mol) of 2-bromo-1-trifluoromethylbenzene in 125 ml of THF is added dropwise. The mixture is stirred for one hour at room temperature and 10.1 g (0.041 mol) of benzylpiperidone are added dropwise. The mixture is stirred for 1 hour at room temperature and a saturated ammonium chloride solution is added. After extraction with ethyl ether, the organic phase is dried and the solvent is evaporated off under reduced pressure. The product is purified by chromatography on a silica gel column using a cyclohexane/ethyl acetate mixture as the eluent to give 6.8 g of 1-benzyl-4-hydroxy-4-(2-tri-fluoromethylphenyl)piperidine, which is hydrogenated with 0.7 g of 10% Pd/C in 75 ml of 95% ethanol which has been brought to acid pH by the addition of hydrochloric acid, the mixture being heated at a temperature of 60° C. for 8 hours. The catalyst is filtered off to give 2.1 g of the title product M.p. 247–251° C.

16b/4-(2-Trnfluoromethylphenyl)-1,2,3,6-tetrahydropyrdine hydrochloride 2.0 g (0.007 mol) of the product of the previous step are dissolved in 12 ml of glacial acetic acid. 3 ml of concentrated sulfuric acid are added dropwise and the mixture is heated at 100° C. for two hours. It is poured onto ice, a concentrated NaOH solution is added until the pH is basic, and the mixture is extracted with methylene chloride. The organic phase is dried and the solvent is evaporated off under reduced pressure. The product is taken up with 15 ml of isopropanol to give 4-(2-trifluoromethylphenyl)-1,2,3,6-tetrahydropyridine. The hydrochloride is prepared with a solution of hydrochloric acid in isopropanol to give 0.9 g of the title compound. M.p. 213–215° C.

16c/1-[2-(3,4-Diethylphenyt)ethyl]-4-(2-tifluoromethylphenyl)-1,2,3,6-tetrahydropyridine hydrochloride 0.4 g (0.0015 mol) of the product of the previous step and 0.52 g (0.0037 mol) of anhydrous $K_2CO_3$ in 12 ml of butanol are refluxed for 30 minutes. 0.41 g (0.0017 mol) of the product obtained in Example la/ is then added and the mixture is refluxed for 6 hours. The solvent is evaporated off, the residue is taken up with ethyl acetate and washed with water, the organic phase is dried and the solvent is evaporated off under reduced pressure. The product is purified by chromatography on a silica gel column using an 8/2 cyclohexane/ethyl acetate mixture as the eluent to give 1-[2-(3,4-diethylphenyl)ethyl]-4(2-trifluoromethylphenyl)-1,2,3,6-etrahydropyridine. The hydrochloride is prepared with a solution of hydrochloric acid in isopropanol to give the title compound. M.p. 184–185° C.

We claim:

1. Compound of formula (I):

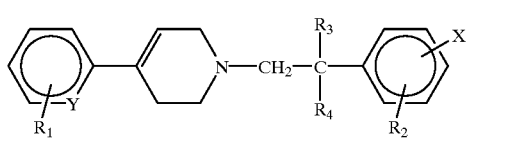

in which:

Y is —CH— or —N—;

$R_1$ is hydrogen, a halogen or a $CF_3$, $(C_1-C_4)$alkyl or $(C_1-C_4)$alkoxy group;

$R_2$ is a methyl or ethyl group;

$R_3$ and $R_4$ are each hydrogen or a $(C_1-C_3)$alkyl; and

X is:

(a) a $(C_1-C_6)$alkyl, a $(C_1-C_6)$alkoxy, a $(C_3-C_7)$ carboxyalkyl, a $(C_1-C_4)$alkoxy-carbonyl$(C_1-C_6)$ allyl, a $(C_3-C_7)$carboxyalkoxy or a $(C_1-C_4)$ alkoxycarbonyl-$(C_1-C_6)$alkoxy;

(b) a radical selected from $(C_3-C_7)$cycloalkyl, (C3–$C_7$) cycloalkoxy, $(C_3-C_7)$-cycloalkylmethyl, $(C_3-C_7)$ cycloalkylamino and cyclohexenyl, it being possible for said radical to be substituted by a halogen, hydroxyl, $(C_1-C_4)$-alkoxy, carboxyl, $(C_1-C_4)$ alkoxycarbonyl, amino or mono- or di-$(C_1-C_4)$-alkylamino; or (c) a group selected from a phenyl, phenoxy, phenylamino, N-$(C_1-C_3)$alkyl-phenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$allyl-amino, $(C_1-C_4)$acylamino, carboxyl, $(C_1-C_4)$alkoxycarbonyl, aminocarbonyl, mono- or di-$(C_1-C_4)$alkylaminocarbonyl, amino $(C_1-C_4)$alkyl, hydroxy$(C_1-C_4)$alkyl or halogeno $(C_1-C_4)$alkyl;

and its salts and solvates and its quaternary ammonium salts.

2. Compound according to claim 1 in which Y is a group —CH— and $R_1$ is $CF_3$.

3. Compound according to claim 1 in which Y is a nitrogen atom and $R_1$ is a chlorine atom.

4. Compound according to claim 1, wherein X is a $(C_1-C_6)$ alkyl group.

5. Compound according to claim 1 in which X is a group (c) where the phenyl is substituted by 1 to 3 halogens, 1 to 3 $CF_3$, 1 to 3 $(C_1-C_4)$alkyl, 1 to 3 $(C_1-C_4$-alkoxy, 1 to 3 cyano, 1 to 3 amino, 1 to 3 mono- or di-$(C_1-C_4)$acylamino, $(C_1-C_4)$acylamino, 1 to 3 carboxyl, 1 to 3 $(C_1-C_4)$ alkoxycarbonyl, 1 to 3 aminocarbonyl, 1 to 3 mono- or di-$(C_1-C_4)$allylaminocarbonyl, 1 to 3 amino-$(C_1-C_4)$alkyl, 1 to 3 hydroxy$(C_1-C_4)$alkyl or 1 to 3 halogeno$(C_1-C_4)$alkyl.

6. Compound according to claim 1 of formula (I'):

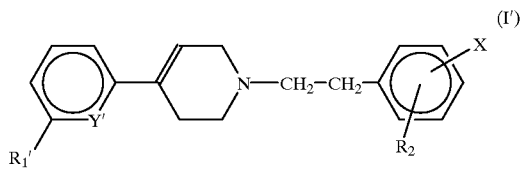

in which $R_1'$ is $CF_3$ and Y' is CH, or $R_1'$ is Cl and Y' is N, $R_2$ and X being as defined for the compounds (I) in claim 1, and its salts, solvates and quaternary ammonium salts.

7. Compound according to claim 6 in which X is a $(C_1-C_6)$alkyl group.

8. Compound according to claim 1 selected from 1-[2-(3,4-diethylphenyl)-ethyl]-4-(3-trifluoromethylphenyl)-1,2,3,6-tetrahydropyridine, 1-[2-(3-methyl-4-pentylphenyl) ethyl]4-(3-trifluoromethylphenyl)-1,2,3,6-tetrahydropyridine, 1-[2-(4methyl-3-pentylphenyl)ethyl ]-4 (3-trifluoromethylphenyl)-1,2,3,6-tetrahydropyridine, 1-[2-(3,4-diethylphenyl)ethyl]-4-(6-chloropyrid-2-yl)-1,2,3,6-tetrahydropyridine and their salts, solvates or quaternary ammonium salts.

9. Method of preparing the compounds of formula (I) according to claim 1, their salts or solvates and their quaternary ammonium salts, characterized in that:

(a) an aryl-1,2,3,6-tetrahydropyridine of formula (II):

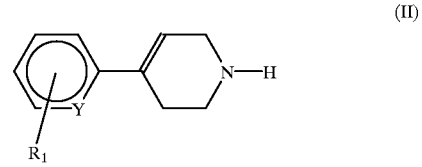

in which Y and $R_1$ are as defined for the compounds (I) in claim 1, is reacted with a compound of formula (III):

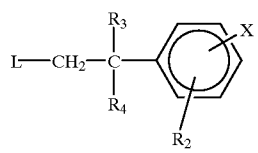

(III)

in which $R_2$, $R_3$, $R_4$ and X are as defined for the compounds (I) in claim 1 and L is a leaving group; and (b) the resulting compound of formula (I) is isolated and optionally converted to one of its salts or solvates or one of its quaternary ammonium salts.

10. Pharmaceutical composition, comprising a compound according to claim 1, or a pharmaceutically acceptable salt thereof.

11. Pharmaceutical composition comprising a compound according to claim 1 and a compound indicated in the symptomatic treatment of senile dementia of the Alzheimer type (DAT), or their pharmaceutically acceptable salts.

12. A method for treating or preventing a disease associated with neuronal degeneration which comprises administering to a patient in need of such treatment a therapeutically effective amount of a compound of formula (I) according to claim 1.

13. A method according to claim 12, wherein the therapeutically effective amount of a compound of formula (I) is between 0.5 and 1400 mg per day.

14. A method according to claim 13, wherein the therapeutically effective amount is between 2 and 200 mg per day.

15. A method according to claim 12, further comprising administering a therapeutically effective amount of a second compound indicated in the treatment of said disease associated with neuronal degeneration.

16. A method according to claim 15, wherein said second compound is chosen from the group consisting of acetylcholinesterase inhibitors, selective M1 cholinomimetics, NMDA antagonists and nootropics.

17. A method according to claim 12, wherein the disease associated with neuronal degeneration is selected from the group consisting of memory disorders, vascular dementia, postencephalitic disorders, postapoplectic disorders, posttraumatic syndromes due to cranial traumatism, disorders deriving from cerebral anoxia, Alzheimer's disease, senile dementia, subcortical dementia, AIDS-related dementia, neuropathies deriving from morbidity or damage to the sympathetic or sensory nerves, cerebral edema, spinocerebellar degenerations and motor neuron degenerations.

18. A method of treating senile dementia of the Alzheimer type (DAT), which comprises administering to a patient in need of such treatment, a therapeutically effective dose of a compound of formula (I) of claim 1 and a therapeutically effective dose of a compound indicated in the symptomatic treatment of DAT, or pharmaceutically acceptable salts thereof.

19. A method according to claim 18, wherein said compounds are administered simultaneously.

20. A method according to claim 19, wherein said compounds are contained in a single pharmaceutical form.

* * * * *

UNITED STATES PATENT AND TRADEMARK OFFICE
CERTIFICATE OF CORRECTION

PATENT NO. : 6,034,090
DATED : March 7, 2000
INVENTOR(S) : Marco Baroni; Rosanna Cardamone; Jacqueline Fournier & Umberto Guzzi Page 1 of 1

It is certified that error appears in the above-identified patent and that said Letters Patent is hereby corrected as shown below:

Column 15, claim 5,
Line 22, "($C_1$-$C_4$-alkoxy" should read -- ($C_1$-$C_4$)alkoxy --;
Line 23, "di-($C_1$-$C_4$)acylamino" should read -- di-($C_1$-$C_4$)alkylamino --;
Line 24, before "($C_1$-$C_4$)alcylamino" insert -- 1 to 3 --;
Line 26, "di-($C_1$-$C_4$)allylaminocarbonyl" should read -- di-($C_1$-$C_4$)alkylaminocarbonyl --;

Column 14, claim 6,
Line 40, "quatemary" should read -- quaternary --.

Signed and Sealed this

Fifth Day of February, 2002

Attest:

Attesting Officer

JAMES E. ROGAN
*Director of the United States Patent and Trademark Office*